(12) United States Patent
Numao et al.

(10) Patent No.: US 8,743,366 B2
(45) Date of Patent: Jun. 3, 2014

(54) LIGHT EMISSION PORTION, PHOTOELECTRIC SMOKE SENSOR, AND SUCTION-TYPE SMOKE SENSING SYSTEM

(75) Inventors: Kanji Numao, Tokyo (JP); Tadayuki Shibuya, Tokyo (JP)

(73) Assignee: Fenwal Controls of Japan, Ltd., Tokyo (JP)

( * ) Notice: Subject to any disclaimer, the term of this patent is extended or adjusted under 35 U.S.C. 154(b) by 13 days.

(21) Appl. No.: 13/702,081

(22) PCT Filed: Aug. 31, 2012

(86) PCT No.: PCT/JP2012/072195
§ 371 (c)(1),
(2), (4) Date: Dec. 5, 2012

(87) PCT Pub. No.: WO2014/033921
PCT Pub. Date: Mar. 6, 2014

(65) Prior Publication Data
US 2014/0063498 A1 Mar. 6, 2014

(51) Int. Cl.
*G01N 21/15* (2006.01)
*G01N 21/05* (2006.01)

(52) U.S. Cl.
USPC .......................................... 356/438; 356/246

(58) Field of Classification Search
CPC ..................................................... G01N 21/534
USPC .................................................. 356/438, 246
See application file for complete search history.

(56) References Cited

U.S. PATENT DOCUMENTS

2009/0021729 A1* 1/2009 Iguchi et al. ................. 356/246
2010/0176957 A1 7/2010 Iguchi et al.

FOREIGN PATENT DOCUMENTS

| JP | 52-119975 | 10/1977 |
| JP | 52-140377 | 10/1977 |
| JP | 04-44196 A | 2/1992 |
| JP | 09-147255 | 6/1997 |
| JP | 10-334362 A | 12/1998 |

OTHER PUBLICATIONS

International Search Report in corresponding International Application No. PCT/JP2012/072195.
First Office Action issued on Aug. 6, 2013 in Japanese Patent Application No. 2012-543395.

* cited by examiner

*Primary Examiner* — Tarifur Chowdhury
*Assistant Examiner* — Md Rahman
(74) *Attorney, Agent, or Firm* — Bacon & Thomas, PLLC

(57) ABSTRACT

The present invention can detect smoke with high accuracy. A light emitting portion is provided with a light emitting element outputting the inspection light with high brightness, the distribution of which is adjusted. A reflection portion collects the inspection light from the light emitting element to the detection region. A diaphragm portion transmits the collected light toward the detection region, while removing light diffused to regions other than the detection region a light shielding portion shields the light diffused to the regions other than the detection region. The light emitting element is provided with a light source outputting the inspection light with high brightness and a parabolic reflective mirror whose curved surface reflects light from the light source toward the detection region, the reflected light being in a doughnut shape in which the center is relatively dark and the periphery is bright.

7 Claims, 6 Drawing Sheets

| ITEM | F11 CURRENT PRODUCT | HIGHER SENSITIVITY (CURRENT LED) | HIGHER SENSITIVITY (NEW LED) | |
|---|---|---|---|---|
| ADL | 108 | 13 | 40 | ADL REDUCED |
| ADH (SMOKE CONCENTRATION) | 147 (5%/m) | 90 (5%/m) | 160 (1%/m) | SIGNAL AMOUNT INCREASED |
| ADH-ADL (SMOKE CONCENTRATION) | 39 (5%/m) | 77 (5%/m) | 120 (1%/m) | CHANGE AMOUNT INCREASED |
| S/N RATIO | 0.37 | 5.93 | 3.0 | NOISE RESISTANCE IMPROVED |
| CHANGE AMOUNT OF 1%/m | 7.8 | 15.4 | 120 | CHANGE AMOUNT INCREASED |

LIGHT EMISSION PORTION, PHOTOELECTRIC SMOKE SENSOR, AND SUCTION-TYPE SMOKE SENSING SYSTEM

TECHNICAL FIELD

The present invention relates to a light emitting portion with improved light emission intensity, a photoelectric smoke sensor using this light emitting portion, and a suction-type smoke sensing system which incorporates this photoelectric smoke sensor.

BACKGROUND ART

The photoelectric smoke sensor is equipment for detecting smoke caused by an outbreak of a fire in a space. Specifically, the photoelectric smoke sensor detects smoke flowing into a housing of the photoelectric smoke sensor by light. Such a photoelectric smoke sensor is installed in an indoor space or a space in various types of devices, and detects smoke in the space.

Photoelectric smoke sensors installed in such a space include a sensor described in Patent Document 1. This photoelectric smoke sensor will be roughly described on the basis of FIG. 1. In the description below, upper, lower, right and left sides are based on the state in FIG. 1.

A smoke sensor 1 is composed of a cylinder portion 2 and a flat box portion 3 extended upward from the cylinder portion 2.

The cylinder portion 2 has functions of allowing intrusion of smoke and guiding the smoke into the inside while preventing entry of ambient light into the inside of the smoke sensor 1. A mountain-shaped labyrinth 4 having a mountain shape (a conical shape with the head part cut off) is provided in a lower-surface opening of the cylinder portion 2. The mountain-shaped labyrinth 4 has its center part raised in a shape of a mountain and has a plurality of openings 5 functioning as an introduction port for the smoke and also preventing entry of the ambient light provided in the peripheral edge portion thereof.

The flat box portion 3 has a substantially rectangular solid shape and has a smoke detection function. A lateral width of the flat box portion 3 is the same as an outer diameter of the cylinder portion 2, and the flat box portion 3 extends upward from the cylinder portion 2 so that the center axis of its own matches the center axis of the cylinder portion 2.

In an upper part of the flat box portion 3, a side-face small hole 7 is provided. This side-face small hole 7 functions as an opening when the smoke is led out from the inside of the smoke sensor 1 to the outside. That is, the smoke introduced into the smoke sensor 1 through the opening 5 of the mountain-shaped labyrinth 4 and the side-face small hole (not shown) of the cylinder portion 2 is led out through the side-face small hole 7 of the flat box portion 3. The smoke might flow into the smoke sensor 1 also through the side-face small hole 7.

Inside of the smoke sensor 1, a light emitting element 8 and a light receiving element 9 are provided.

The light emitting element 8 is an element provided by being faced with a detection region AR in the housing of the flat box portion 3 and emitting inspection light to the detection region AR. The light emitting element 8 is provided at a position in an upper part of an internal space of the flat box portion 3 (upper left in FIG. 1) by a light emitting element accommodation portion 11. The light emitting element accommodation portion 11 accommodates the light emitting element 8 so that the inspection light emitted from the light emitting element 8 is emitted only forward. An optical window portion 12 is provided in front of the light emitting element accommodation portion 11.

The light receiving element 9 is provided at a position in the lower left in the internal space of the flat box portion 3 by a light receiving element accommodation portion 13. The light receiving element accommodation portion 13 accommodates the light receiving element 9 in a bottom portion thereof and has an objective lens 14 attached in an upper part thereof.

The light receiving element 9 is provided by being faced with the detection region AR at a position shifted from an optical path of the inspection light of the light emitting element 8 and receives diffused light which is the inspection light diffused by having hit the smoke and detects the smoke. Specifically, the optical axis of the light emitting element 8 and the optical axis of the light receiving element 9 are configured to cross each other at an angle of approximately 120 degrees, and the vicinity of the intersection becomes the smoke detection region AR. As a result, if there is smoke in the detection region AR, the inspection light from the light emitting element 8 is diffused by the smoke, the diffused light reaches the light receiving element 9, and the presence of the smoke is detected.

Between the light emitting element 8 and the light receiving element 9 (at a position left to the detection region AR), a shielding plate 15 is provided for preventing direct entry of the inspection light from the light emitting element 8 into the light receiving element 9 without being diffused.

In the right of the light receiving element accommodation portion 13, two labyrinth pieces 17 and 18 are provided. The labyrinth piece 17 is formed with inclination in an upper right direction and guides an air flow from the lower side to the upper right direction by its lower surface. Moreover, an end portion in the upper direction of the labyrinth piece 17 is bent to an upper left direction. This end portion has a function of leading the air flow raised along an upper face toward the detection region AR. The labyrinth piece 18 is formed with inclination in an upper left direction at a position upper left of the labyrinth piece 17. The labyrinth piece 18 guides the air flow directly from below and the air flow flowing along the inclination of a lower inclined surface 13a of the light receiving element accommodation portion 13 to the upper left direction. In the upper left direction of the labyrinth piece 18, an upper inclined surface 13b of the light receiving element accommodation portion 13 is provided. The air flow flowing toward the upper inclined surface 13b of the light receiving element accommodation portion 13 is directed to the direction of the detection region AR by the inclined surface 13b.

At a lower end position of the side-face small hole 7 of the flat box portion 3, a labyrinth piece 20 extending substantially to the left is provided. This labyrinth piece 20 is bent at the intermediate position thereof so as to be directed to the upper left direction. The air flow having passed the detection region AR and further rising is narrowed by an upper inclined surface 11a of the light emitting element accommodation portion 11 and the lower inclined surface of the labyrinth piece 20 and reaches the upper surface of the internal space. Then, it is directed toward the side-face small hole 7 by a pressure of the air flow after that and is led out of the side-face small hole 7. Reference numeral 21 denotes an insect screen. Moreover, a labyrinth piece 22 is provided below the labyrinth piece 17.

The above-described mountain-shaped labyrinth 4, the lower inclined surface 13a of the light receiving element accommodation portion 13, the labyrinth pieces 17, 18, 20, and 22 and the like suppress entry of the ambient light into the inside.

By means of the above configuration, the inspection light from the light emitting element 8 is emitted to the detection region AR. At this time, direct incidence of the inspection light into the light receiving element 9 is prevented by the shielding plate 15. The ambient light tries to intrude through the opening 5 of the mountain-shaped labyrinth or the side-face small hole 7, but this ambient light is prevented by the labyrinth pieces 17, 18, 20, and 22 and the like.

If smoke intrudes through the opening 5 of the mountain-shaped labyrinth or the side-face small hole 7 in this state, the smoke intrudes into the detection region AR through the labyrinth pieces 17, 18, 20, and 22 and the like. Then, the presence of the smoke is detected when the inspection light from the light emitting element 8 is diffused by the smoke, and the diffused light reaches the light receiving element 9.
Patent Document: International Publication No. WO2006-112085

DISCLOSURE OF THE INVENTION

Problems to be Solved by the Invention

By means of the above-described prior-art photoelectric smoke sensor, smoke caused by a fire can be detected, but if concentration of the smoke is low, detection becomes difficult. That is, if the smoke intrudes the detection region AR, the inspection light from the light emitting element 8 is diffused by the smoke, the diffused light reaches the light receiving element 9, and the presence of the smoke is detected, but if the concentration of the smoke is low, a diffused amount of the inspection light becomes small, and detection becomes difficult.

Thus, a photoelectric smoke sensor which can sense smoke with higher accuracy than the prior-art photoelectric smoke sensor is in demand.

The present invention was made in view of the above-described circumstances, and a light emitting portion, a photoelectric smoke sensor, and a suction-type smoke sensing system which can detect smoke with higher accuracy are provided.

Means to Solve the Problems

In order to solve the above-described problems, a light emitting portion of the present invention is provided with, in a light emitting portion which collects inspection light in a detection region, a light emitting element outputting the inspection light with high brightness whose brightness distribution is adjusted, a reflection portion provided on the detection region side of the light emitting element and collecting the inspection light from the light emitting element to the above-described detection region, a diaphragm portion provided on the detection region side of the reflection portion and transmitting the inspection light traveling toward the detection region and to remove light diffused to regions other than the detection region, and a light shielding portion provided on the detection region side of the diaphragm portion and shielding the light diffused to the regions other than the detection region, the light emitting element being provided with a light source outputting the inspection light with high brightness and a parabola reflective mirror whose curved surface is set so that light from the light source is reflected and becomes the inspection light toward the detection region, and the curved surface of the parabola reflective mirror emits light in a circular shape as a whole by means of the inspection light and emits light in a doughnut shape in which the center of the circle is relatively dark and the periphery is bright.

The photoelectric smoke sensor and the suction-type smoke sensing system of the present invention have their characterized portions similar to those of the above-described light emitting portion.

Effect of the Invention

According to the present invention, smoke can be detected with high accuracy.

Figure 1:
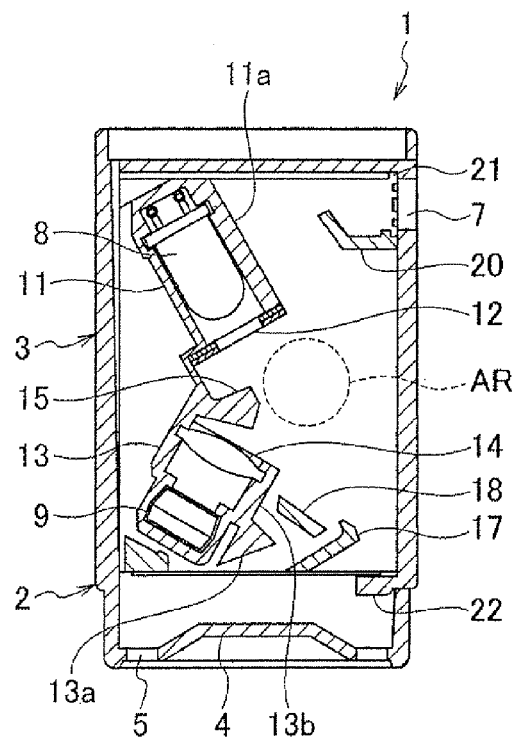
FIG. 1 is a side sectional view illustrating a prior-art photoelectric smoke sensor.

EXPLANATIONS OF REFERENCE NUMERALS 3 flat box portion
3a housing
3b detection-region side inner wall
9 light receiving element
32, 33 reflecting member
32a, 33a reflecting surface
34 light emitting portion
36 light emitting element
37 reflection portion
37a reflecting surface
38 diaphragm portion
38a reflecting surface
39 light shielding portion
39a reflecting surface
41 light source
42 parabola reflective mirror
AR detection region

BEST MODE FOR CARRYING OUT THE INVENTION

A light emitting portion, a photoelectric smoke sensor, and a suction-type smoke sensing system of the present invention will be described below. The photoelectric smoke sensor using the light emitting portion of the present invention and the suction-type smoke sensing system using this photoelectric smoke sensor are a highly sensitive photoelectric smoke sensor and a suction-type smoke sensing system which can be installed in a semiconductor manufacturing device in a factory, a machine tool, a power distribution panel, an industrial controller, a device or the like in which a fire can break out in a place where people gather such as a general household, a public facility and the like. Particularly, this is a photoelectric smoke sensor and a suction-type smoke sensing system suitably installed in a place where slight smoke needs to be detected at high sensitivity in a special environment such as a clean room. The photoelectric smoke sensor incorporating the light emitting portion of the present invention will be first described below, and then, the suction-type smoke sensing system incorporating this photoelectric smoke sensor will be described.

(A) Photoelectric Smoke Sensor

First, the photoelectric smoke sensor according to this embodiment will be described. Characteristics of the photoelectric smoke sensor according to this embodiment are in a light emitting portion and a reflecting member. The photoelectric smoke sensor of this embodiment has a configuration as a whole substantially similar to that of the above-described prior-art photoelectric smoke sensor. Thus, the same reference numerals are given to the same members and the description thereof will be omitted. In the photoelectric smoke sensor of this embodiment, a small hole 24 is provided in an upper surface instead of the prior-art side-face small hole 7. Moreover, if the photoelectric smoke sensor is specifically installed, there are other necessary configurations in addition to the configuration described in this embodiment, but since they are all known configurations, they are omitted here.

Figure 2:
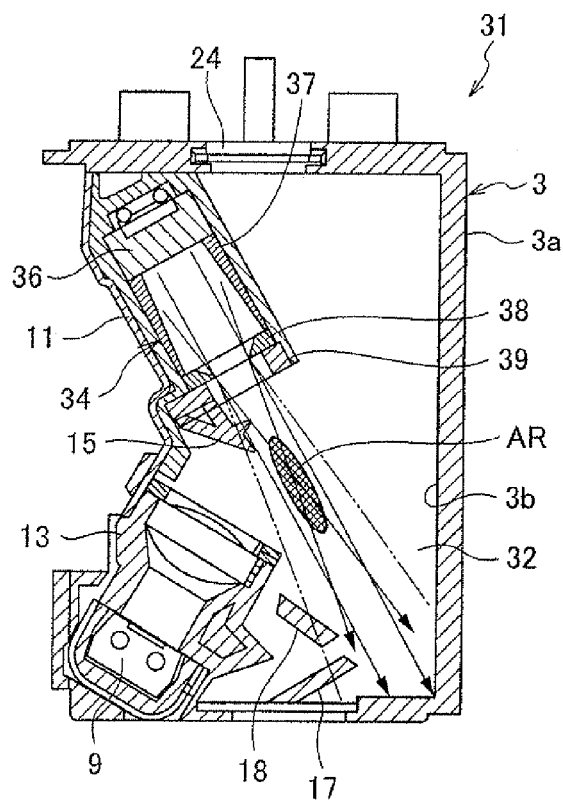
FIG. 2 is a side sectional view illustrating a photoelectric smoke sensor according to an embodiment of the present invention.
Figure 3:
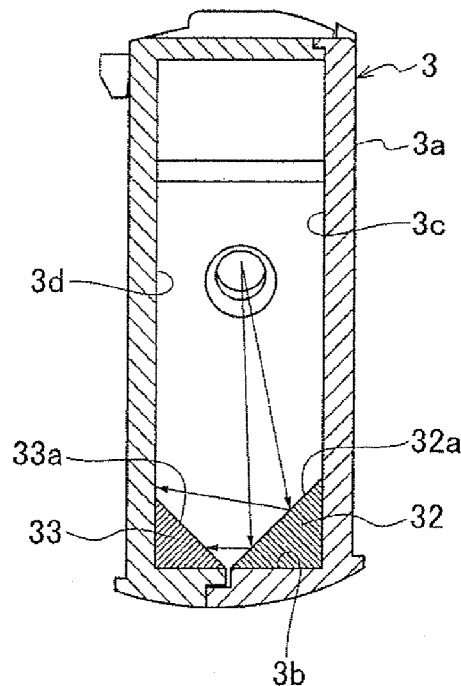
FIG. 3 is a plan sectional view of FIG. 2.

First, improvement of control of reflected light will be described below. Reflecting members 32 and 33 are provided in a photoelectric smoke sensor 31 as illustrated in FIGS. 2 and 3 for control of the reflected light. These reflecting members 32 and 33 are members deflecting inspection light emitted from a light emitting portion 34 from the light receiving element 9 and to reflect the light so that the inspection light does not enter the light receiving element 9. The reflecting members 32 and 33 are provided on a detection-region side inner wall 3b of a housing 3a at positions opposite to the light emitting portion 34 with the detection region AR between them. The reflecting members 32 and 33 are provided on the whole region in the vertical direction of the detection-region side inner wall 3b as illustrated in FIG. 2. Further, the reflecting members 32 and 33 are provided with reflecting surfaces 32a and 33a, each being inclined having a V-shaped planar shape, as illustrated in FIG. 3. These reflecting surfaces 32a and 33a are surfaces deflecting the inspection light emitted from the light emitting portion 34 from the light receiving element 9 in a direction not directed toward the light receiving element 9 and to reflect the light. The reflecting surface 32a is formed larger than the reflecting surface 33a. The reflecting surface 32a is provided on one side wall surface 3c side of the housing 3a and occupies a wider area. The reflecting surface 33a is provided on the other side wall surface 3d side of the housing 3a and occupies an area smaller than the reflecting surface 32a. As a result, the inspection light emitted from the light emitting portion 34 is reflected irregularly by the two reflecting surfaces 32a and 33a. By reflecting the inspection light irregularly by the two reflecting surfaces 32a and 33a, the reflected light is reflected in a direction not directed toward the light receiving element 9 (deflected from the light receiving element 9) as illustrated in FIG. 3. Areas and inclination angles of the two reflecting surfaces 32a and 33a are set so that the reflected light is not directed toward the light receiving element 9 in relation with the light emitting portion 34.

Some light in the reflected light is reflected twice by the V-shaped reflecting surfaces 32a and 33a and thus changing the direction by 180 degrees. However, if the inspection light is reflected twice, brightness is drastically attenuated, and a light amount is drastically decreased. Therefore, even if the reflected light reflected twice (secondary reflected light) enters the light receiving element 9, it becomes extremely weak light and does not cause a problem.

Moreover, the portions other than the above-described configuration are not particularly limited. The configuration that can be incorporated in the photoelectric smoke sensor 31 of this invention (peripheral configuration of the existing photoelectric smoke sensor) can be all applied to the present invention.

Figure 4:
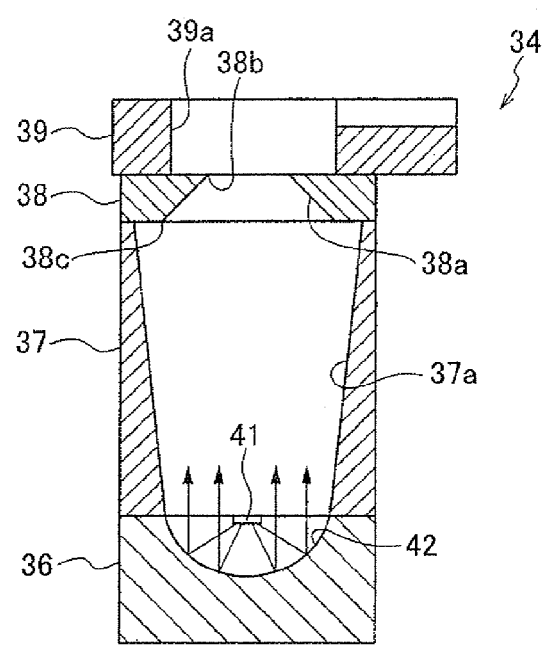
FIG. 4 is a side sectional view illustrating a light emitting portion of the photoelectric smoke sensor of the embodiment of the present invention.

The light emitting portion 34 has been improved so that the (high brightness) inspection light with high light emission intensity is efficiently collected to the detection region AR. In the case of the photoelectric smoke sensor 31, as in Table in FIG. 5 which will be described later, the larger a difference between ADL (minimum value of AD converted value) and ADH (maximum value of AD converted value) is, the higher the sensitivity of the sensor becomes. The difference between ADL and ADH cannot be increased by simply raising the light emission intensity of the light emitting portion 34, since the value of ADL becomes high. The light emitting portion 34 of this embodiment has improved this point. This light emitting portion 34 is mainly composed of a light emitting element 36, a reflection portion 37, a diaphragm portion 38, and a light shielding portion 39 as shown in FIG. 4.

The light emitting element 36 is a member for outputting the inspection light with high brightness whose brightness distribution is adjusted. This light emitting element 36 is composed of a high brightness light source 41 and a parabola reflective mirror 42. The light source 41 uses a high brightness chip LED or the like. The light from the light source 41 such as the high brightness chip LED or the like is adjusted by the parabola reflective mirror 42. A curved surface of the parabola reflective mirror 42 is set such that the light from the light source 41 is reflected and becomes the substantially parallel inspection light toward the detection region AR. Specifically, the light source 41 and the curved surface of the parabola reflective mirror 42 are set such that the inspection light emitted from the light emitting element 36 is reflected substantially in parallel and the high brightness portion becomes a doughnut shape. That is, the light source 41 and the curved surface of the parabola reflective mirror 42 are set such that, if the emitted light (inspection light) irradiates a plane disposed on the optical axis extending to the detection region AR on the emission side of the parabola reflective mirror 42 and at a position opposite to this parabola reflective mirror 42, the light is emitted in a circular shape as a whole and also emitted in a doughnut shape in which the center of the circle is relatively dark and the periphery is bright.

The reflection portion 37 is a member for collecting the inspection light from the light emitting element 36 to the detection region AR. The reflection portion 37 is formed of a cylindrical member. An inner side face of this cylindrical reflection portion 37 is a reflecting surface 37a. This reflecting surface 37a is composed of a conical shape (conical surface) expanding to an emitting direction (the detection region AR side) of the inspection light. An inclination angle of this conical reflecting surface 37a is set to an angle at which the inspection light from the light emitting element 36 having the above-described doughnut-shaped high brightness portion is collected to the detection region AR. The reflection portion 37 is attached to the emitting side (the detection region AR side) of the light emitting element 36. The reflection portion 37 uses a material having a large reflection damping amount such as black ABS resin or the like. The diaphragm portion 38 and the light shielding portion 39 also use the similar material.

The diaphragm portion 38 is a member for transmitting the inspection light traveling toward the detection region AR and to remove the light diffused to the regions other than the detection region AR. The diaphragm portion 38 is attached to the emission side (detection region AR side) of the reflection portion 37. The diaphragm portion 38 is provided with a conical (conical surface) reflecting surface 38a expanding in a direction opposite to the reflection portion 37. An inclination angle of this conical reflecting surface 38a is set so that the inspection light collected to the detection region AR by the reflection portion 37 is transmitted as it is and the light diffused to the regions other than the detection region AR is reflected into the reflection portion 37 and the like. Specifically, a small diameter portion 38b on the detection region AR side in the diaphragm portion 38 has substantially the same size as that of the detection region AR and a diameter is set to substantially the same diameter of a light flux of the inspection light collected to the detection region AR by the reflection portion 37. As a result, the diaphragm portion 38 transmits the inspection light not reflected by the reflection portion 37 in the inspection light emitted from the parabola reflective mirror 42 and directly irradiates the detection region AR. That is, it is configured such that the inspection light having passed through the small diameter portion 38b of the diaphragm portion 38 without being reflected by the reflection portion 37 in the inspection light emitted from the parabola reflective mirror 42 directly irradiates the detection region AR.

A large diameter portion 38c is set so that the inclination angle of the reflective surface 38a becomes an angle by which the light diffused to the regions other than the detection region AR is reflected. Specifically, if the light diffused to the regions other than the detection region AR enters the reflecting surface 38a, a diameter of the large diameter portion 38c is set so as to have an angle by which the reflected light is reflected by the opposite reflecting surface 38a or the light shielding portion 39. Since the angle of this reflecting surface 38a is different depending on conditions such as performances of the light emitting element 36, a dimension of the reflection portion 37 and the like, it is set in relation to the light emitting element 36 and the reflection portion 37.

The light shielding portion 39 is a member for shielding the light diffused to the regions other than the detection region AR. The light receiving portion 39 is provided on the emission side (detection region AR side) of the diaphragm portion 38. The light shielding portion 39 has a cylindrical reflecting surface 39a formed inside thereof. An inner diameter of this reflecting surface 39a is set to a diameter larger than the small diameter portion 38b of the diaphragm portion 38. The inner diameter and a height of this reflecting surface 39a of this light shielding portion 39 are set to the dimension such that the light diffused to the regions other than the detection region AR which is the light reflected by the reflecting surface 37a of the reflecting portion 37 and the light reflected by the reflecting surface 38a of the diaphragm portion 38 can be shielded. Specifically, the dimension is set so that the light expanding at a wide angle in the light transmitted through the diaphragm portion 38 can be shielded.

Since the light entering the light shielding portion 39 is light reflected by the reflection portion 37 or the diaphragm portion 38 at least once, the light reflected by the light shielding portion 39 is light reflected twice or more. Thus, the light reflected by the light shielding portion 39 is drastically attenuated and becomes weak. Even if this weak light is diffused to the regions other than the detection region AR, it does not cause any problem. As a result, the ADL (the minimum value of AD converted value) can be kept low.

The photoelectric smoke sensor 31 configured as above works as follows.

In the light emitting portion 34, the light from the light source 41 of the light emitting element 36 is adjusted by the parabola reflective mirror 42 and is emitted to the detection region AR side as the substantially parallel reflected light (inspection light). The inspection light having passed through the small diameter portion 38b of the diaphragm portion 38 without being reflected by the reflection portion 37 in the inspection light emitted from the parabola reflective mirror 42 directly irradiates the detection region AR. Since this inspection light is not attenuated by the reflection, it becomes strong light.

The inspection light hit and reflected by the reflecting surface 38a of the diaphragm portion 38 is reflected again by the reflecting surface 38a (the surface on the side opposite to the annular reflecting surface 38a) opposite to this reflecting surface 38a, is drastically attenuated and returns into the reflection portion 37 or is reflected by the reflecting surface 39a of the light shielding portion 39 and is drastically attenuated.

The inspection light expanded to the periphery in the inspection light emitted from the parabola reflective mirror 42 is reflected by the reflecting surface 37a of the reflection portion 37, is transmitted through the small diameter portion 38b of the diaphragm portion 38, and irradiates the detection region AR. The inspection light hit and reflected by the reflecting surface 38a of the diaphragm portion 38 is reflected again by the reflecting surface 38a (the surface on the side opposite to the annular reflecting surface 38a) opposite to this reflecting surface 38a, is drastically attenuated and returns into the reflection portion 37 or is reflected by the reflecting surface 39a of the light shielding portion 39 and is drastically attenuated.

At this time, since the inspection light emitted from the parabola reflective mirror 42 of the light emitting element 36 has a high brightness portion having a doughnut-shape, this doughnut-shaped high brightness inspection light is reflected by the reflecting surface 37a of the reflection portion 37, passes through the small diameter portion 38b of the diaphragm portion 38 and irradiates the detection region AR.

As a result, the inspection light directly irradiated and the inspection light reflected by the reflection portion 37 and irradiated are overlapped in the detection region AR. As a result, the strong inspection light can be efficiently collected in the detection region AR. Moreover, since the reflecting surface 37a of the reflection portion 37 is long, the inspection light reflected by this reflecting surface 37a is also collected deeper (longer) on the optical axis. As a result, the strong inspection light can be efficiently collected in the whole region of the detection region AR. Therefore, the detection region AR at high sensitivity with a large difference between the ADL and the ADH is constructed.

On the other hand, the inspection light emitted from the parabola reflective mirror 42 of the light emitting element 36 toward the detection region AR is transmitted through the detection region AR and irradiates the reflecting members 32 and 33. Moreover, there is also the inspection light irradiating the side wall surfaces 3c and 3d, but this light is reflected by the side wall surfaces 3c and 3d and irradiates the reflecting members 32 and 33.

In the reflecting members 32 and 33, the light is irregularly reflected by the V-shaped reflecting surfaces 32a and 33a so as to eliminate the reflected light toward the light receiving element 9. A part of the reflected light goes toward the light receiving element 9, but such light has been reflected twice or more as described above and drastically attenuated, thus not causing any problem.

The reflected light reflected by the reflecting surfaces 32a and 33a irradiates the opposite reflecting surfaces 33a and 32a or the side wall surfaces 3c or 3d. Most of the reflected light reflected by the reflecting surfaces 33a and 32a irradiates the side wall surfaces 3c and 3d and is reflected by these side wall surfaces 3c and 3d. Moreover, most of the reflected light reflected by the side wall surfaces 3c and 3d irradiates the opposite side wall surfaces 3c and 3d and is reflected again. As a result, the reflected light of the inspection light gathers around the detection region AR and repeats reflection and rarely enters the light receiving element 9.

If smoke intrudes from the outside and reaches the vicinity of the detection region AR in this state, the inspection light from the light emitting portion 34 hits the smoke and is diffused, the diffused light enters the light receiving element 9, and the smoke is detected. At this time, since the strong inspection light gathers in the whole region of the detection region AR, strong diffused light is generated by the smoke having intruded the detection region AR. Furthermore, since the reflected light is distributed also around the detection region AR, the diffused light is also generated in this portion, thereby increasing the diffused light in the housing 3a of the flat box portion 3.

As a result, entry of the reflected light which becomes noise into the light receiving element 9 can be drastically decreased, and the diffused light by the smoke can be increased. Thus, the light receiving element 9 can detect the smoke with higher accuracy. As a result, the photoelectric smoke sensor 31 of this embodiment can be made into a highly sensitive smoke sensor with a large difference between ADL and ADH.

(B) Example

Subsequently, an experiment result using the above-described photoelectric smoke sensor 31 will be described in comparison with the prior-art photoelectric smoke sensor.

As the light emitting element 36 of the photoelectric smoke sensor 31 in this example, an element provided with the performances discussed below was used. That is, a light emitting element having an output of 70 mW, a forward voltage of 1.5 V, and a pulse forward current of 2 A was used.

Moreover, as a light emitting element of the prior-art photoelectric smoke sensor, a light emitting element having an output of 24 mW, a forward voltage of 1.45 V, and a pulse forward current of 50 mA was used. As a result, the light emitting element 36 of this example has a light amount increased from that of the prior-art light emitting element.

Moreover, as the light receiving element 9 of the photoelectric smoke sensor of this example, an element provided with the performances discussed below was used. That is, a light receiving element having performances such that a peak sensitivity wavelength is 940 nm, a color temperature is 2856 K, an open voltage when an EV display value of a standard tungsten bulb is at 1000 Lx is 0.35 V, and a short-circuit current is 75 µA was used.

As the light receiving element of the prior-art photoelectric smoke sensor, a light receiving element similar to the light receiving element 9 of the above-described example was also used.

By using these photoelectric smoke sensors, a smoke experiment was conducted at the respective detection concentrations (%/m). The result of this experiment is shown in Table in FIG. 5. Here, three types of the photoelectric smoke sensors, that is, the prior-art photoelectric smoke sensor, a photoelectric smoke sensor in which the current light emitting element (LED) is attached to the flat box portion 3 provided with the reflecting members 32 and 33 of the present invention, and the photoelectric smoke sensor 31 of this example were used in the experiment.

Figures 5, 6:
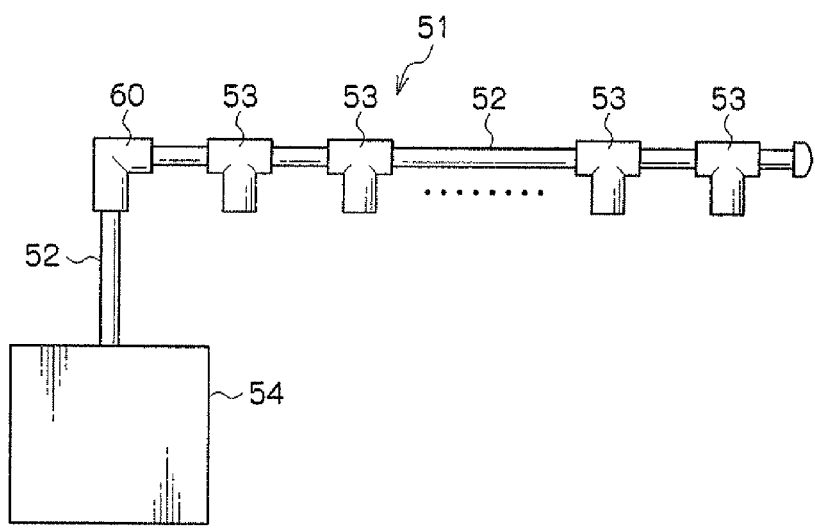
FIG. 5 is a table illustrating an experiment result according to an example of the present invention.
FIG. 6 is a configuration diagram illustrating a suction-type smoke sensing system according to the embodiment of the present invention.

In Table in FIG. 5, ADL (minimum value of AD converted value) at 108 in the prior-art photoelectric smoke sensor was reduced to 13 in the current photoelectric smoke sensor using the flat box portion 3 of the present invention. The value was 40 in the photoelectric smoke sensor 31 of this example, which indicates drastic reduction from the prior-art photoelectric smoke sensor. That is, by using the light emitting portion 34 of the above-described configuration, light which becomes noise was kept low, and a light amount could be increased. As a result, in the photoelectric smoke sensor of this example, the ADL could be drastically reduced as compared with the prior-art photoelectric smoke sensor.

Moreover, ADH (maximum value of AD converted value) at 147 in the prior-art photoelectric smoke sensor was reduced to 90 in the current photoelectric smoke sensor using the flat box portion 3 of the present invention. The value was 160 in the photoelectric smoke sensor 31 of this example. As a result, a signal amount could be increased as compared with the prior-art product.

As a result, the ADH−ADL rose from 39 in the prior-art photoelectric smoke sensor to 77 in the current photoelectric smoke sensor using the flat box portion 3 of the present invention. In the photoelectric smoke sensor 31 of this example, the value was 120. If the value is converted to a change amount in 1%/m, the value at 7.8 in the prior-art photoelectric smoke sensor rose to 15.4 in the current photoelectric smoke sensor using the flat box portion 3 of the present invention. The value was 120 in the photoelectric smoke sensor 31 of this example. As a result, the change amount was drastically increased as compared with the prior-art product. Furthermore, S/N ratio at 0.37 in the prior-art photoelectric smoke sensor rose to 5.93 in the current photoelectric smoke sensor using the flat box portion 3 of the present invention. The value was 3.0 in the photoelectric smoke sensor 31 of this example. As a result, in the photoelectric smoke sensor 31 of this example, noise resistance was drastically improved as compared with the prior-art photoelectric smoke sensor.

As a result, the current photoelectric smoke sensor using the flat box portion 3 of the present invention senses smoke at sensitivity higher than that of the prior-art photoelectric smoke sensor, and it is known that the photoelectric smoke sensor 31 of this example senses smoke at drastically higher sensitivity. The photoelectric smoke sensor 31 of this example particularly has an ADH−ADL value much higher than that of the current photoelectric smoke sensor using the flat box portion 3 of the present invention, and it is known that the smoke is sensed at high sensitivity.

As a result, the photoelectric smoke sensor 31 of this example can sense smoke at high sensitivity.

(C) Suction-Type Smoke Sensing System

Subsequently, the suction-type smoke sensing system of the present invention will be described. This suction-type smoke sensing system is a system incorporating the above-described photoelectric smoke sensor 31.

The suction-type smoke sensing system of the present invention is a system which specifies a region to be inspected and senses smoke in the region with high accuracy and rapidly. This suction-type smoke sensing system sucks air in each region to be inspected, respectively, and senses smoke when sucking the air.

A suction-type smoke sensing system 51 mainly includes, as illustrated in FIG. 6, a sampling pipe 52, a photoelectric smoke sensing portion 53, and a control unit 54. If the suction-type smoke sensing system 51 is specifically installed in each region to be inspected, a configuration other than the above-described configuration may be required, but since they are all known configurations, explanation will be omitted here. The same applies to the following.

The sampling pipe 52 is a pipe disposed facing the region to be inspected for sucking air in this region to be inspected. The sampling pipe 52 is disposed in accordance with the region to be inspected. The number of the regions to be inspected might be one or plural. The sampling pipe 52 is disposed in accordance with these regions to be inspected. The sampling pipe 52 is formed of a pipe member having a plurality of lengths.

Moreover, a suction pipe 59 (See FIG. 9) might be provided from the sampling pipe 52 to the region to be inspected. As a result, the sampling pipe 52 is assembled on each fitting port 58 of the photoelectric smoke sensing portion 53 which will be described later and the suction pipe 59 is connected to a suction port 57 of the photoelectric smoke sensing portion 53 as appropriate into a piping configuration in accordance with the various regions to be inspected.

There are various piping configurations of this sampling pipe 52 and one of them is an L-shaped piping configuration as illustrated in FIG. 6. The sampling pipe 52 is connected to the both sides of an L-shaped connection pipe 60 and is bent in the L-shape so as to have the L-shaped piping configuration. A control unit 54 is connected to the sampling pipe 52 on the base end side of the connection pipe 60. The sampling pipe 52 and the photoelectric smoke sensing portion 53 are connected alternately to the distal end side of the connection pipe 60. Specifically, the sampling pipe 52 is connected to each fitting port 58 of the photoelectric smoke sensing portion 53 so as to configure the piping in accordance with the region to be inspected. The sampling pipe 52 might be connected longer in accordance with the region to be inspected. The connection pipe 60 or connection pipes having other angles might be used at the distal end side of the connection pipe 60 so as to cause the sampling pipe 52 to meander in accordance with the region to be inspected.

Figure 8:
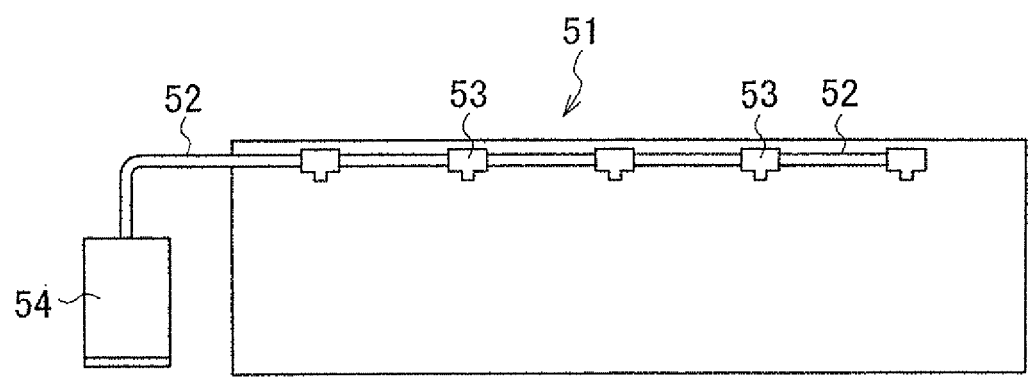
FIG. 8 is a configuration diagram illustrating a piping configuration example of the suction-type smoke sensing system of the present invention.

Moreover, if the region to be inspected is a large space as illustrated in FIG. 8, a plurality (5 units in FIG. 8) of the photoelectric smoke sensing portion 53 are installed by being connected with the sampling pipe 52 at certain intervals.

Figure 9:
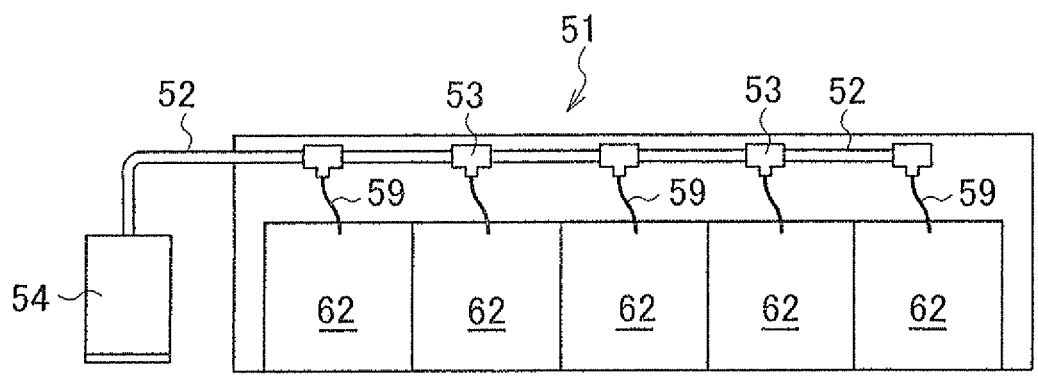
FIG. 9 is a configuration diagram illustrating a piping configuration example of the suction-type smoke sensing system of the present invention.

Moreover, if the region to be inspected is divided into small spaces 62 such as power receiving facilities disposed in plural as in FIG. 9, the suction pipe 59 is connected to the suction port 57 of each of the photoelectric smoke sensing portions 53, and each suction pipe 59 is extended into each space 62.

Figure 10:
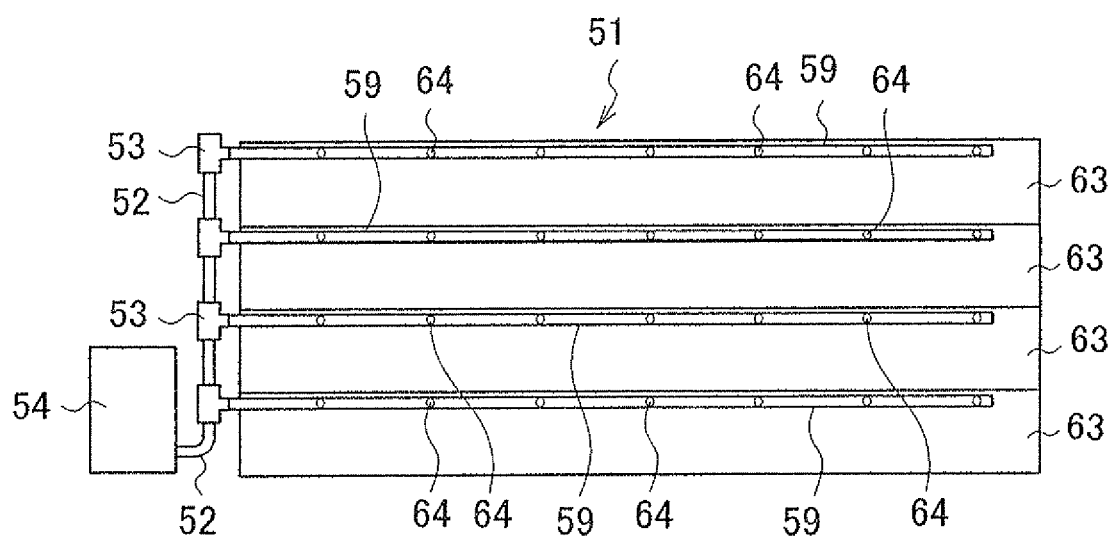
FIG. 10 is a configuration diagram illustrating a piping configuration example of the suction-type smoke sensing system of the present invention.

If the region to be inspected is configured by stacking laterally-wide and vertically-small spaces 63 in plural stages as in FIG. 10, the photoelectric smoke sensing portion 53 is disposed so as to be located respectively in each space 63. Specifically, each photoelectric smoke sensing portion 53 is connected by the sampling pipe 52 to each other, the suction pipe 59 is connected to the suction port 57 of each photoelectric smoke sensing portion 53, respectively, and each suction pipe 59 is disposed in each space 63. In each suction pipe 59, air inlets 64 are provided at certain intervals.

Other than the above, various piping configurations are possible. That is, various piping configurations can be realized by arranging each of the photoelectric smoke sensing portion 53 in accordance with the region to be inspected and by connecting these photoelectric smoke sensing portion 53 and the control unit 54 by the sampling pipe 52 as appropriate.

The photoelectric smoke sensing portion 53 is an apparatus which senses mixing of smoke in air when the control unit 54 sucks the air in each region to be inspected via the sampling pipe 52. The photoelectric smoke sensing portion 53 is attached to the sampling pipe 52 while being faced with each of the above-described regions to be inspected. Moreover, the photoelectric smoke sensing portion 53 has a function as connecting means for connecting a plurality of the sampling pipes 52 constituting the piping of the suction-type smoke sensing system 51 as appropriate. An address is set to each of the photoelectric smoke sensing portion 53, respectively. The control unit 54 can accurately identify the position of each photoelectric smoke sensing portion 53 by this address. As means for setting an address to each of the photoelectric smoke sensing portion 53, any of the known means can be used.

Figure 7:
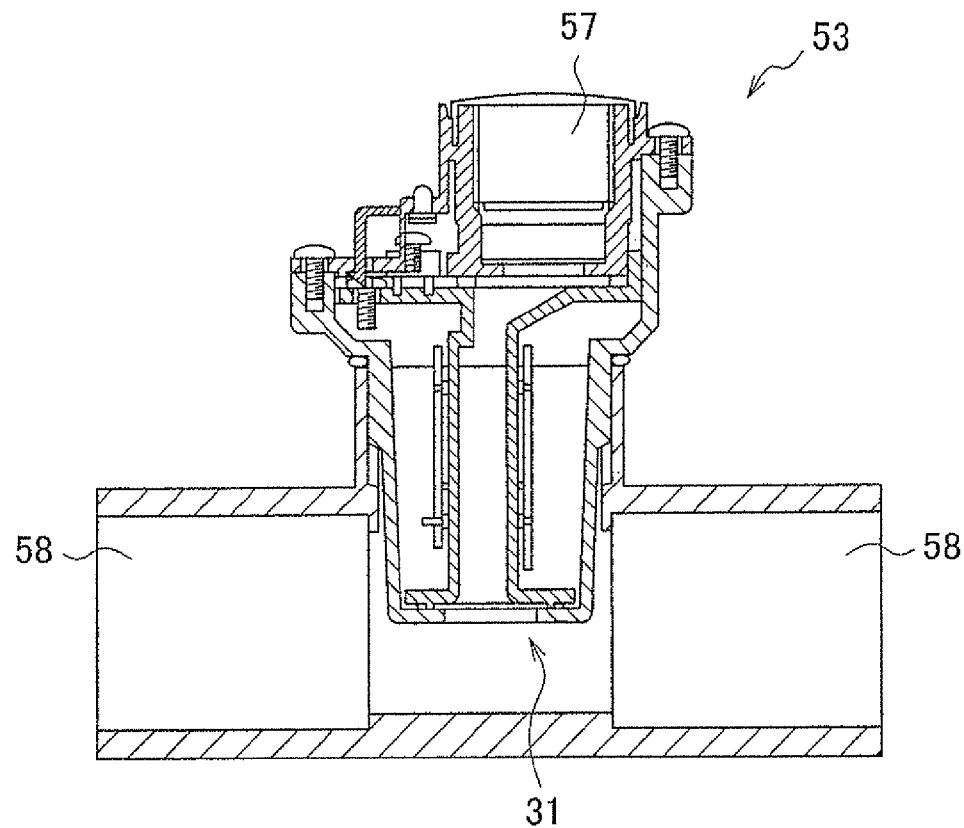
FIG. 7 is a sectional view illustrating a photoelectric smoke sensing portion according to the embodiment of the present invention.

The photoelectric smoke sensing portion 53 mainly includes, as illustrated in FIG. 7, the photoelectric smoke sensor 31, the suction port 57, and the fitting port 58.

The photoelectric smoke sensor 31 is an apparatus described above. In FIG. 2, only an arranged position of this photoelectric smoke sensor 31 is specified, and specific configuration of the photoelectric smoke sensor 31 is omitted.

The suction port 57 is an opening for directly sucking the air in the region to be inspected. Moreover, the suction port 57 is an opening for fitting the base end portion of the suction pipe 59 disposed by being extended to the region to be inspected. This suction port 57 is provided on the air inflow side of the photoelectric smoke sensor 31.

The suction port 57 is formed cylindrically, and one of ends thereof is opened. This suction port 57 is provided so as to open toward the region to be inspected and sucks the peripheral air. If the suction pipe 59 is fitted in the suction port 57, the air around the distal end opening of this suction pipe 59 is sucked. The suction port 57 is connected to the photoelectric smoke sensor 31. As a result, when the air is sucked from the photoelectric smoke sensor 31 side, the air in the periphery of the suction port 57 or the periphery of the distal end opening of the suction pipe 59 is sucked and flows into the photoelectric smoke sensor 31.

The fitting port 58 is an opening which fits in the end portion of the sampling pipe 52 so as to create the piping configuration of the suction-type smoke sensing system 51. The fitting port 58 is provided on the air outflow side of the photoelectric smoke sensor 31. The fitting port 58 might be provided singularly on the air outflow side of the photoelectric smoke sensor 31 but two fitting ports are provided oppositely here. The sampling pipe 52 is connected to these two fitting ports 58 as appropriate. Moreover, the suction pipe 59 is connected to the suction port 57 as appropriate. As a result, the piping configuration in accordance with various regions to be inspected as illustrated in FIGS. 8 to 10 can be assembled.

The control unit 54 is a device which mainly sucks the air in the region to be inspected and processes a detection signal. The control unit 54 might be provided with other functions but is mainly provided with the above two functions here. That is, the control unit 54 is mainly provided with functions as a suction apparatus (not shown) which is connected to the base end portion of the sampling pipe 52 and sucks air in the region to be inspected and a smoke detecting apparatus which is electrically connected to the photoelectric smoke sensing portion 53 and detects presence of smoke by receiving a detection signal. The control unit 54 is electrically connected to a light receiving element 18 of the photoelectric smoke sensor 31 of the photoelectric smoke sensing portion 53. Specifically, a signal line (not shown) is disposed separately from the sampling pipe 52, and the light receiving element 18 of each photoelectric smoke sensor 31 and the control unit 54 are electrically connected. As a result, the control unit 54 grasps the position of each photoelectric smoke sensor 31. The control unit 54 can adjust the sensitivity by changing the threshold value in accordance with the detection signal.

Moreover, portions other than the above-described configuration are not particularly limited. Configurations which can be incorporated in the photoelectric smoke sensor of the present invention (peripheral configuration of conventional photoelectric smoke sensors) can be all applied to the present invention.

The suction-type smoke sensing system 51 configured as above acts as follows.

The control unit 54 is operated, and air in the region to be inspected is sucked from the suction port 57 through the sampling pipe 52. If the suction pipe 59 is connected to the suction port 57, the air inside the power distribution panel or the like is sucked from the distal end of the suction pipe 59. The sucked air flows into the photoelectric smoke sensor 31.

In the photoelectric smoke sensor 31, if smoke intrudes from the outside and reaches the vicinity of the detection region AR, the inspection light from the light emitting portion 34 hits the smoke and is diffused, and the diffused light enters the light receiving element 9 and the light receiving element 9 detects the smoke. At this time, since the reflected light is also distributed in the periphery of the detection region AR, the diffused light is also generated in this portion, and the diffused light in the housing 3 increases.

As a result, incidence of the reflected light which becomes noise into the light receiving element 9 can be drastically decreased, and at the same time, the diffused light by the smoke can be increased. Thus, the light receiving element 9 can sense the smoke with higher accuracy.

If a threshold value of the photoelectric smoke sensor 31 is raised so as to lower the sensitivity, the smoke is sensed when a large quantity of smoke is generated by fire.

When the photoelectric smoke sensor 31 senses the smoke, a detection signal is transmitted to the control unit 54. Since the control unit 54 knows the position of the photoelectric smoke sensing portion 53 which sensed the smoke by the address, upon reception of the detection signal, the control unit 54 identifies outbreak of fire and the position of the fire. And the control unit 54 displays or transmits the outbreak of the fire and positional information as necessary.

As a result, the photoelectric smoke sensor 31 with high sensitivity according to the situation of the region to be inspected can discover fire at an early stage by detecting presence of smoke immediately in the region to be inspected.

With a smoke sensing system using a prior-art sampling pipe, if the number of sampling holes is increased, it takes time from generation of smoke to detection of smoke as the smoke is diluted. Moreover, if the piping length of the sampling pipe is long, it takes time for the smoke to reach the smoke sensor, and detection time is delayed. For example, when alarm sensitivity was set to 0.2%/m and 30 sampling holes were provided as an example of the smoke sensing system, smoke was not sensed and an alarm was not issued even at the closest location to the smoke sensor until smoke with concentration of 0.75%/m was sucked through 6 holes. At the terminal end portion farthest from the smoke sensor, the number of holes required for sensing the smoke and issuing the alarm was further increased. Particularly, in the case of the whole piping length of 45 m, 8 holes were required for issuing an alarm, and it took an extremely long time of 1 minute and 20 seconds to sense the smoke.

On the other hand, with the suction-type smoke sensing system 51 of this embodiment, since the sampling holes in the sampling pipe are replaced by the photoelectric smoke sensor 31, it becomes possible to directly sense the smoke by the neighboring photoelectric smoke sensor 31 in a site where smoke was generated. Thus, there is no problem of dilution of smoke caused by an increase in the number of sampling holes or delay in detection time caused by prolongation of the piping length of the sampling pipe. However longer the sampling pipe is formed, there is no problem of delay in the detection time. Moreover, since each of the photoelectric smoke sensors 31 has its own address, the spot where the smoke is generated can be easily identified.

That is, smoke can be detected with high accuracy and rapidly and a spot of fire outbreak can be identified.

Moreover, if the region to be inspected is a factory or the like, for example, where some smoke can be generated in a usual work, appropriate smoke detection according to the situation of the region to be inspected becomes possible by raising the above-described threshold value so as to lower the sensitivity of the photoelectric smoke sensor 31.

As a result, smoke can be detected with high accuracy and rapidly and a fire outbreak spot can be identified while the device is kept small to the size of the conventional photoelectric smoke sensor.

(D) Variation

Figure 11:
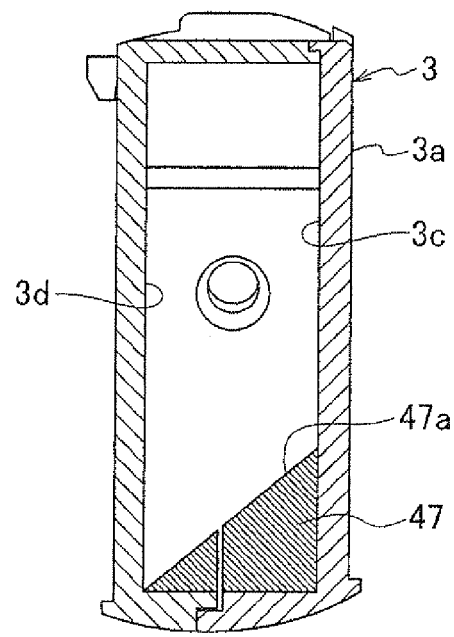
FIG. 11 is a plan sectional view of the photoelectric smoke sensor according to a first variation of the present invention.

In the above-described embodiment, the V-shaped reflecting surfaces 32a and 33a are provided by the reflecting members 32 and 33, but as illustrated in FIG. 11, one reflecting surface 47a can be provided by one large reflecting member 47. As a result, the inspection light is reflected by the reflecting surface 47a and all irradiates the side wall surface 3d and is reflected by this side wall surface 3d. Then, secondary reflected light is drastically attenuated. Therefore, the detection light from the light emitting portion can be reflected in a direction not directed to the light receiving portion. In this case, too, the actions and effects similar to those in the above-described embodiment can be exerted.

Figure 12:
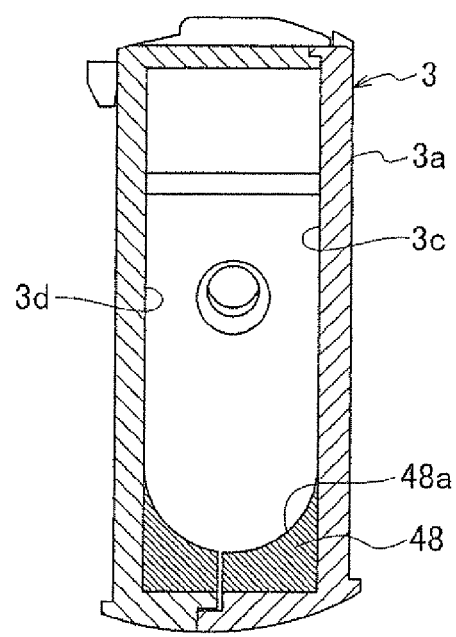
FIG. 12 is a plan sectional view of the photoelectric smoke sensor according to a second variation of the present invention.

Moreover, as illustrated in FIG. 12, a curved reflecting surface 48a may be provided by the reflecting member 48. Furthermore, the reflecting surface 48a may be formed so that the reflected light gathers in the detection region AR and its periphery like a concave mirror of a reflecting telescope. By this reflecting surface 48a, the detection light from the light emitting portion can be reflected in the direction gathering in the detection region. That is, the reflecting surface 48a may be configured to be curved so that the inspection light and the reflected light gather in the detection region AR and its periphery and more diffused light by the smoke flowing into the housing 3a can be generated. In this case, the reflecting surface 48a may be formed as a mirror surface. By forming the reflecting surface 48a as a mirror surface, more reflected light can be gathered to the detection region AR and its periphery.

By these configurations, smoke can be detected with higher accuracy.

The invention claimed is:

1. A light emitting portion which collects inspection light in a detection region, comprising:
   a light emitting element outputting the inspection light with high brightness whose brightness distribution is adjusted;
   a reflection portion provided on the detection region side of the light emitting element and collecting the inspection light from the light emitting element to the detection region;
   a diaphragm portion provided on the detection region side of the reflection portion and transmitting the inspection light traveling toward the detection region and to remove light diffused to regions other than the detection region; and
   a light shielding portion provided on the detection region side of the diaphragm portion and shielding the light diffused to the regions other than the detection region, wherein
   the light emitting element is provided with a light source outputting the inspection light with high brightness and a parabola reflective mirror whose curved surface is set so that light from the light source is reflected and becomes the inspection light toward the detection region; and
   the curved surface of the parabola reflective mirror is set so as to emit light in a circular shape as a whole by means of the inspection light and to emit light in a doughnut shape in which the center of the circle is relatively dark and the periphery is bright,
   wherein the diaphragm portion allows the inspection light not reflected by the reflection portion in the inspection light emitted from the parabola reflective mirror to pass therethrough and to directly irradiate the detection region; and
   wherein the reflection portion has a conical reflecting surface expanded to the detection region side; and an inclination angle of the reflecting surface is set to an angle at which the inspection light having the doughnut-shaped high brightness portion is collected in the detection region.

2. A photoelectric smoke sensor which detects smoke flowing into a housing by light, comprising:
   a light emitting portion provided by being faced with a detection region in the housing and emitting inspection light to the detection region;
   a light receiving element provided at a position shifted from an optical path of the inspection light of the light emitting portion by being faced with the detection region and receiving diffused light which is the inspection light having hit the smoke and to detect the smoke; and
   a reflecting member provided in the housing and deflecting and reflecting the inspection light emitted from the light emitting portion so as not to enter the light receiving element, wherein
   the light emitting portion is provided with a light emitting element outputting the inspection light with high brightness whose brightness distribution is adjusted; a reflection portion provided on the detection region side of the light emitting element and collecting the inspection light from the light emitting element to the detection region; a diaphragm portion provided on the detection region side of the reflection portion and transmitting the inspection light traveling toward the detection region and to remove light diffused to regions other than the detection region; and a light shielding portion provided on the detection region side of the diaphragm portion and shielding the light diffused to the regions other than the detection region;
   the light emitting element is provided with a light source outputting the inspection light with high brightness and a parabola reflective mirror whose curved surface is set so that light from the light source is reflected and becomes the inspection light toward the detection region; and
   the curved surface of the parabola reflective mirror is set so as to emit light in a circular shape as a whole by means of the inspection light and to emit light in a doughnut shape in which the center of the circle is relatively dark and the periphery is bright.

3. The photoelectric smoke sensor according to claim 2, wherein
   the reflecting member is provided at a position opposite to the light emitting portion and the light receiving element while sandwiching the detection region and reflecting the inspection light from the light emitting portion in a direction not directed to the light receiving element.

4. The photoelectric smoke sensor according to claim 2, wherein
   the reflecting member is provided at a position opposite to the light emitting portion and the light receiving element while sandwiching the detection region and reflecting the inspection light from the light emitting portion in a direction gathering to the detection region.

5. A suction-type smoke sensing system comprising:
   a piping which is disposed, facing one or a plurality of regions to be inspected, and sucks air in each of the regions to be inspected;
   a photoelectric smoke sensing portion which is attached to the piping in a state facing each of the regions to be inspected and detects smoke mixed in the air when the air in each of the regions to be inspected is sucked; and
   a control unit which is connected to a base end portion of the piping and sucks the air in the region to be inspected and is electrically connected to the photoelectric smoke sensing portion so as to receive and process a detection signal, wherein
   the photoelectric smoke sensing portion is provided with a photoelectric smoke sensor which senses smoke in the sucked air, a suction port provided on an air inflow side of the photoelectric smoke sensor, directly sucking the air in the region to be inspected and fitted with the base end portion of a suction pipe extending to the region to be inspected, and a fitting port provided on an air outflow side of the photoelectric smoke sensor and fitted with an end portion of the piping;
   the photoelectric smoke sensor is provided with a light emitting portion provided by being faced with the detection region in the housing and emitting the inspection light to the detection region; a light receiving element provided at a position shifted from an optical path of the inspection light of the light emitting portion by being faced with the detection region and receiving diffused light which was the inspection light having hit the smoke and diffused and to detect the smoke; and a reflecting member provided in the housing and deflecting and reflect the inspection light emitted from the light emitting portion so as not to enter the light receiving element;
   the light emitting portion is provided with a light emitting element outputting the inspection light with high brightness whose brightness distribution is adjusted; a reflection portion provided on the detection region side of the light emitting element and collecting the inspection light from the light emitting element to the detection region; a diaphragm portion provided on the detection region side of the reflection portion and transmitting the inspection light traveling toward the detection region and to remove light diffused to regions other than the detection region; and a light shielding portion provided on the detection region side of the diaphragm portion and shielding the light diffused to the regions other than the detection region;

the light emitting element is provided with a light source outputting the inspection light with high brightness and a parabola reflective mirror whose curved surface is set so that light from the light source is reflected and becomes the inspection light toward the detection region; and the curved surface of the parabola reflective mirror is set so as to emit light in a circular shape as a whole by means of the inspection light and to emit light in a doughnut shape in which the center of the circle is relatively dark and the periphery is bright.

6. The suction-type smoke sensing system according to claim 5, wherein two pieces of the fitting ports of the photoelectric smoke sensing portion are provided oppositely; and the piping is connected to each of the fitting ports and the suction pipe is connected to the suction port as appropriate so as to assemble a piping configuration according to various regions to be inspected.

7. The suction-type smoke sensing system according to claim 5, wherein the control unit identifies a position of fire outbreak from positional information of the photoelectric smoke sensing portion which is a transmitting source of a received detection signal.

* * * * *